United States Patent
Heaton et al.

(10) Patent No.: US 6,703,832 B2
(45) Date of Patent: Mar. 9, 2004

(54) METHOD FOR DETECTING HYDROCARBONS BY COMPARING NMR RESPONSE AT DIFFERENT DEPTHS OF INVESTIGATION

(75) Inventors: Nicholas J. Heaton, Houston, TX (US); Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/065,983

(22) Filed: Dec. 6, 2002

(65) Prior Publication Data

US 2004/0027122 A1 Feb. 12, 2004

Related U.S. Application Data

(60) Provisional application No. 60/319,462, filed on Aug. 12, 2002.

(51) Int. Cl.$^7$ ................................................. G01V 3/00
(52) U.S. Cl. ........................................ 324/303; 324/300
(58) Field of Search .............................. 324/303, 300, 324/309, 307; 335/296

(56) References Cited

U.S. PATENT DOCUMENTS

| | | | |
|---|---|---|---|
| 3,597,681 A | 8/1971 | Huckabay ................ 324/303 |
| 5,055,788 A | 10/1991 | Kleinberg et al. ......... 324/303 |
| 5,486,762 A | * 1/1996 | Hreedman et al. ......... 324/303 |
| 6,121,774 A | 9/2000 | Sun et al. ................. 324/303 |
| 6,140,817 A | 10/2000 | Flaum et al. ............. 324/303 |
| 6,166,543 A | 12/2000 | Sezginer et al. .......... 324/303 |
| 6,229,308 B1 | 5/2001 | Freedman ................ 324/303 |
| 6,232,778 B1 | 5/2001 | Speier et al. ............. 324/303 |
| 6,255,818 B1 | 7/2001 | Heaton et al. ............ 324/303 |
| 6,400,147 B1 | 6/2002 | Toufaily et al. ........... 324/303 |
| 6,459,992 B1 | 10/2002 | Freedman et al. ......... 324/303 |
| 6,498,484 B1 | 12/2002 | Sun et al. ................. 324/303 |
| 6,518,757 B1 | 2/2003 | Speier ..................... 324/303 |

(List continued on next page.)

FOREIGN PATENT DOCUMENTS

| | | |
|---|---|---|
| GB | 2 342 170 A * | 8/1999 |
| WO | WO 01/42817 A1 | 6/2001 |

OTHER PUBLICATIONS

WFJ Slijkerman et al., "Processing of Multi–Acquisition NMR Data," *SPE 56768 SPE Annual Technical Conference and Exhibition* (Houston, TX Oct. 3–6, 1999).

(List continued on next page.)

*Primary Examiner*—Diego Gutierrez
*Assistant Examiner*—Brij B. Shrivastav
(74) *Attorney, Agent, or Firm*—Kevin P. McEnaney; Brigitte L. Jeffery; John J. Ryberg (57) ABSTRACT

A method for detecting hydrocarbon-bearing zones in a formation penetrated by a wellbore includes acquiring at least two nuclear magnetic resonance measurements, each of the at least two nuclear magnetic resonance measurements acquired from a volume of investigation at a different radial depth from the wellbore; and determining whether the formation bears hydrocarbons by comparing the at least two nuclear magnetic resonance measurements. A method for detecting fines invasion in a formation surrounding a wellbore includes acquiring at least two nuclear magnetic resonance measurements, each of the at least two nuclear magnetic resonance measurements acquired from a volume of investigation at a different radial depth from the wellbore; and determining whether the fines invasion has occurred by comparing the at least two nuclear magnetic resonance measurements.

26 Claims, 6 Drawing Sheets

U.S. PATENT DOCUMENTS

| | | | |
|---|---|---|---|
| 6,522,137 B1 | 2/2003 | Sun et al. | 324/303 |
| 6,522,138 B2 | 2/2003 | Heaton | 324/303 |
| 6,534,980 B2 | 3/2003 | Toufaily et al. | 324/303 |
| 6,559,638 B1 | 5/2003 | Adelerhof | 324/303 |
| 6,573,716 B2 | 6/2003 | Toufaily et al. | 324/303 |

OTHER PUBLICATIONS

R. Freedman et al., "Field Applications of a New Nuclear Magnetic Resonance Fluid Characterization Method," *SPE 71713 SPE Annual Technical Conference and Exhibition* (New Orleans, LA Sep. 30 —Oct. 3, 2001).

NJ Heaton et al., "Applications of a New–Generation Wireline NMR Logging Tool," *SPE 77400 SPE Annual Technical Conference and Exhibition* (San Antonio, TX Sep. 29 –Oct. 2, 2002).

R. Freedman et al., "A New NMR Method of Fluid Characterization in Reservoir Rocks: Experimental Confirmation and Simulation Results," *SPE Journal* (Dec. 2001).

MD Hurlimann, et al., "Diffusion–Editing: New NMR Measurement of Saturation and Pore Geometry," *SPWLA $43^{rd}$ Annual Logging Symposium* (Jun. 2–5, 2002).

* cited by examiner

METHOD FOR DETECTING HYDROCARBONS BY COMPARING NMR RESPONSE AT DIFFERENT DEPTHS OF INVESTIGATION

CROSS REFERENCE TO RELATED APPLICATIONS

This invention claims the benefit of U.S. Provisional Application serial no. 60/319,462 filed on August 12, 2002.

BACKGROUND OF INVENTION

1. Field of the Invention

The present invention relates to the field of well logging. More specifically, the present invention relates to methods for detecting hydrocarbons in reservoirs and fines invasion into formations using nuclear magnetic resonance measurements.

2. Background Art

Oil and gas exploration and production are very expensive operations. Any knowledge about the formations that can help reduce the unnecessary waste of resources in well drilling will be invaluable. Therefore, the oil and gas industry have developed various tools capable of determining and predicting earth formation properties. Among different types of tools, nuclear magnetic resonance (NMR) instruments have proven to be invaluable. NMR instruments can be used to determine formation properties, such as the fractional volume of pore space and the fractional volume of mobile fluid filling the pore space. General background of NMR well logging is described in U.S. Patent No. 6,140,817.

Nuclear magnetic resonance is a phenomenon occurring in a selected group of nuclei having magnetic nuclear moments, i.e., non-zero spin quantum numbers. $^1$H (proton) is the species commonly detected in NMR well logging because of its natural abundance and sensitivity to NMR measurements. When these nuclei are placed in a magnetic field ($B_o$, "Zeeman field"), they each precess around the axis of the $B_0$ field with a specific frequency, the Larmor frequency ($\omega_o$), which is a characteristic property of each nuclear species (gyromagnetic ratio, $Y$) and depends on the magnetic field strength ($B_0$) effective at the location of the nucleus, i.e., $\omega_0 = Y B_0$.

Both water and hydrocarbons in the formations produce NMR signals that are detected in well logging. It is desirable that the signals from water and hydrocarbons be separable so that one can identify which regions in the formations have hydrocarbons. However, it is not always easy to distinguish which signals are from water and which are from hydrocarbons. Various methods have been proposed to separately identify water and hydrocarbon signals.

Current NMR methods of hydrocarbon detection may be divided in two categories. The simplest methods involve making a small number of measurements (typically 2) in which just one of the measurement parameters is changed. The difference between the measurements is then interpreted on the basis of known or assumed models for the NMR response of different fluids. The most common techniques of this type are Differential Spectrum (polarization time, WT, is changed) and Shifted Spectrum/Enhanced Diffusion (echo spacing, TE, is changed). These methods take advantages of the fact that water and hydrocarbons often have different relaxation times ($T_1$ and/or $T_2$) and diffusion constants. These methods are outlined in U.S. Pat. No. 6,229,308 B1 issued to Freedman ("the Freedman patent") and references cited therein. The Freedman patent is assigned to the assignee of the present invention and is hereby incorporated by reference.

The second category of NMR hydrocarbon detection methods is more general and applies forward modeling to suites of NMR data acquired with different parameters, typically TE and WT, although in principle the gradient, G, may also be included as a parameter. There are currently two methods of this type: MACNMR (Slijkerman et al. 1999, SPE 56768) and MRF as disclosed in the Freedman patent.

These NMR hydrocarbon detection methods compare measurements that are made in the same or similar volumes of investigation. When this is not the case, it is nonetheless assumed that all data acquired in the measurement suite may be described by a single set of fluid saturations. None of these methods has exploited variations in NMR response from different depths of investigation.

During well drilling, a fluid (drilling fluid or mud) is pumped into the well. The drilling fluid serves to remove the cuttings from the well and to cool the cutting surfaces of drill bits. The drilling fluids can be water-based muds or oil-based muds. These drilling fluids are typically pumped at high pressure in order to prevent formation fluids from gushing into the well before the well is completed. Because the drilling fluids are at higher pressures than the formation pressures, these fluids may filter into the formation mud filtrate invasion. In addition, fines suspended in the drilling muds may also invade the formation. As used herein, fines refers to very small particles either in muds or mud additives. The extent to which drilling fluids or fines invade the formation depends on several factors: the formation permeability, the pressure differential between the borehole fluids and the formation, the mud type, and the time elapsed since the hole was drilled. Due to the variations in these parameters, the invasion fronts may occur at distances ranging from a few millimeters to several feet into the formation.

The invasion of drilling fluids into the formations is a nuisance for many well logging operations. One either has to sample the formations far away from the wellbore, hoping that the mud filtrate does not reach the region of investigation, or to have a way of differentiating the signals of the mud filtrate from those of the formation fluids. Similarly, invasion of fines from the drilling muds into the formation results in heterogeneity in the vicinity of the borehole. These fine particles can physically plug or bridge across flowpaths in the porous formation, leading to formation damage.

While data processing methods such as the MRF method are capable of separating the mud filtrate components from other components in the NMR measurements, these are post acquisition methods. It is desirable to have NMR logging methods that can take advantage of the mud invasion, instead of at odds with the mud invasion, so that the presence of hydrocarbons in the formation can be easily identified. In addition, it is desirable to have methods for detecting fines invasion.

SUMMARY OF INVENTION

One aspect of the invention relates to methods for detecting the presence of hydrocarbons in earth formations. A method for detecting hydrocarbon-bearing zones in a formation penetrated by a wellbore includes acquiring at least two nuclear magnetic resonance measurements, each of the at least two nuclear magnetic resonance measurements acquired from a volume of investigation at a different radial depth from the wellbore; and determining whether the formation bears hydrocarbons by comparing the at least two nuclear magnetic resonance measurements.

Another aspect of the invention relates to methods of well logging. A method for nuclear magnetic resonance logging of a formation penetrated by a wellbore includes providing a nuclear magnetic resonance instrument moveable in the wellbore; acquiring at least two nuclear magnetic resonance measurements, each of the at least two nuclear magnetic resonance measurements acquired at a volume of investigation at a different radial depth from the wellbore; and determining whether the formation bears hydrocarbons by comparing the at least two nuclear magnetic resonance measurements.

Another aspect of the invention relates to methods for detecting fines invasion. A method for detecting fines invasion in a formation surrounding a wellbore includes acquiring at least two nuclear magnetic resonance measurements, each of the at least two nuclear magnetic resonance measurements acquired from a volume of investigation at a different radial depth from the wellbore; and determining whether the fines invasion has occurred by comparing the at least two nuclear magnetic resonance measurements.

Other aspects and advantages of the invention will be apparent from the following description and the appended claims.

DETAILED DESCRIPTION

The invention relates to methods for detecting hydrocarbons in reservoirs based on comparison of NMR measurements obtained at different volumes located at different distances from the borehole surface. The new generation wireline and while-drilling NMR tools are capable of investigation at various depth into the formation. Embodiments of the invention are applicable when the invasion front occurs within the range of the NMR measurement volumes or when the invasion front travels beyond the range of the NMR measurement volumes because the mud filtrate forms a gradient across different radial depths of investigation or generates a non-uniform distribution of fluids spanning the range of the DOIs.

Figures 1, 2:
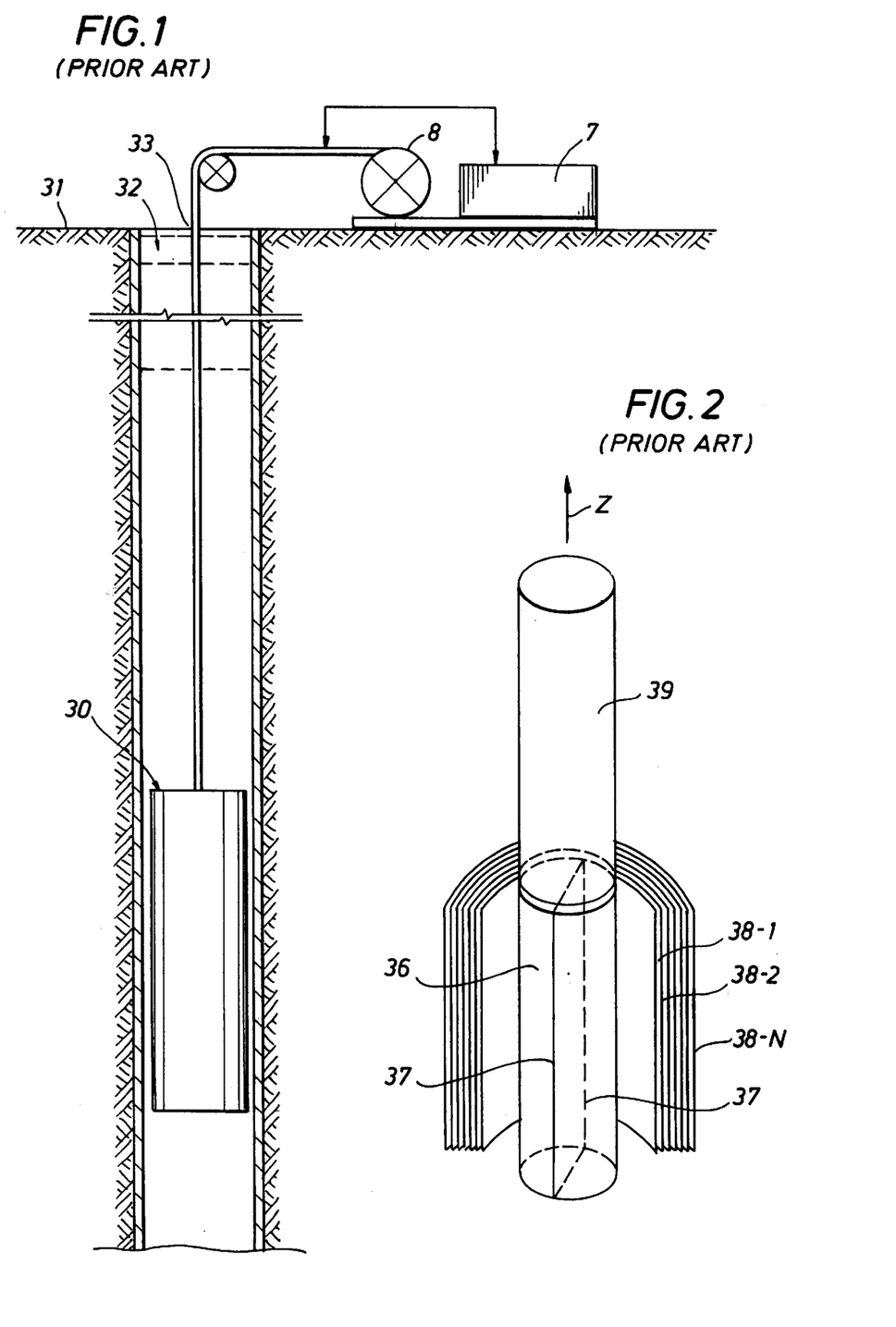
FIG. 1 illustrates a nuclear magnetic resonance logging system.
FIG 2. illustrates a nuclear magnetic resonance instrument capable of multi-frequency detection.

FIG. 1 illustrates a schematic of an NMR logging system. In FIG. 1, a nuclear magnetic resonance (NMR) logging tool 30 for investigating earth formations 31 traversed by a borehole 32 is shown. The NMR logging device 30 is suspended in the borehole 32 on an armored cable 33, the length of which substantially determines the relative axial depth of the device 30. The cable length is controlled by suitable means at the surface such as a drum and winch mechanism 8. Surface equipment 7 can be of conventional type and can include a processor subsystem which communicates with downhole equipment including NMR logging device 30.

The NMR logging device 30 can be any suitable nuclear magnetic resonance logging device; it may be one for use in wireline logging applications as shown in FIG. 1 ;or one that can be used in logging-while-drilling (LWD) or measurement-while-drilling (MWD) applications. The NMR logging device 30 typically includes a means for producing a static magnetic field in the formations, and a radio frequency (RF) antenna means for producing pulses of magnetic field in the formations and for receiving the spin echoes from the formations. The means for producing a static magnetic field may comprise a permanent magnet or magnet array, and the RF antenna means for producing pulses of magnetic field and receiving spin echoes from the formations may comprise one or more RF antennas.

A variety of NMR logging tools that may be used with methods of the present invention are known in the art. FIG. 2 illustrates a schematic of some of the components of one type of NMR logging device 30. FIG. 2 shows a first centralized magnet or magnet array 36 and an RF antenna 37, which may be a suitably oriented coil or coils. FIG. 2 also illustrates a general representation of closely-spaced cylindrical thin shells, 38-1, 38-2 . . . 38-N, that can be frequency selected in a multi-frequency logging operation. One such device is disclosed in U.S. Pat. No. 4,710,713. In FIG. 2, another magnet or magnet array 39 is shown. Magnet array 39 maybe used to pre-polarize the earth formation ahead of the investigation region as the logging device 30 is raised in the borehole in the direction of arrow Z. Examples of such devices include those disclosed in U.S. Pat. Nos. 5,055,788 and 3,597,681.

Embodiments of the invention provide methods for detecting the presence of hydrocarbon by observing variations in NMR responses at different distances from the borehole (different radial depth of investigation). Any variation is then related to differences in fluid saturations, in particular native hydrocarbon saturation, which may arise from invasion of drilling fluid into the formation. To detect fluid saturations, several NMR parameters may be used, including longitudinal relaxation time ($T_1$), transverse relaxation time ($T_2$), ratio of $T_1/T_2$, diffusion constant (D), and magnetic field gradient (G). These parameters affect the magnitudes of NMR signals by different mechanisms.

Carr-Purcell-Meiboom-Gill (CPMG) pulse sequence is the most common pulse sequence in NMR well logging. The magnitude of an NMR signal measured with a CPMG sequence in the presence of a field gradient can be described as:

$$F(t, WT, TE, G) = C(G) \cdot \Phi \cdot \quad (1)$$

$$\sum_j S_j H_j \sum_k a_{j,k}\left(1 - e^{-WT/T1_{j,k}}\right) \cdot e^{-t/T2_{j,k}} \cdot e^{-(GTE)^2 \gamma^2 D_{j,k} t/12}$$

where F(t, Wt, TE, C) is the signal amplitude at time t(for the nth echo, t=n×TE) for a measurement with WT, TE and G; C(G) is a porosity calibration factor that may be different for each magnetic field gradient (G); $\phi$ is the formation porosity; $S_j$ is the saturation of fluid j; $H_j$ is the hydrogen index of fluid j; $a_{j,k}$ is the amplitude of signal from the k-th component of fluid j; WT is the effective polarization time of a CPMG measurement; $T1_{j,k}$ is the longitudinal relaxation time for the k-th component of fluid j; $T2_{j,k}$ is the transverse relaxation time for the k-th component of fluid j; G is the magnetic field gradient resulted from the tool magnet; TE is the inter-echo delay time in a CPMG pulse sequence; Y is the proton gyromagnetic ratio; and $D_{j,k}$ is the diffusion constant for the k-th component of fluid j.

Equation (1) is valid for standard CPMG sequences and assumes that the field gradient is uniform in the NMR measurement volume. It also assumes unrestricted diffusion and the absence of any significant internal gradients in the formation. One skilled in the art would appreciate that alternative expressions could readily be formulated in which these assumptions were not imposed. However, equation (1) suffices for most situations and does not imply any loss of generality of the method. Similar expressions could equally be found to describe the NMR responses to other pulse sequence, such as the diffusion-editing (DE) spin echo pulse sequence proposed in H u rlimann et al, "Diffusion-Editting: New NMR Measurement of Saturation and Pore Geometry," paper presented at the 2002 Annual Meeting of the Society of Professional Well Log Analysts, Osio, Japan, Jun. 2–5, 2002. This DE pulse sequence would also be applicable to the method described here.

As stated above, prior art NMR hydrocarbon detection methods use differential measurements from the same or similar volumes in the formation and assume the measurements may be described by a single set of fluid saturations. In contrast, embodiments of the invention detect variable fluid saturations in different measurement volumes. The different fluid saturations may arise from invasion of the mud filtrate. Methods of the invention take advantage of the fact that modern NMR logging tools either inherently have magnetic field gradients or have gradient capabilities the regions farther away from the magnet experience lower magnetic fields than do those regions closer to the tool.

As a result of the magnetic field gradient, hydrogen nuclei resonate at different Larmor frequencies (because $\omega_0 = Y B_0$) at different distances from the wellbore. Thus, one can measure different volumes at different DOI using different RF frequencies. In other words, the volumes of investigation may be selected by specific measurement frequencies. At lower measurement frequencies, the volume of investigation is farther from the tool, i.e., deeper into the formation. If the invasion front happens to lie between the volumes probed by two (or more) NMR measurements made in an acquisition suite, the NMR data will reflect possible differences in the fluid saturations (fluid compositions) corresponding to these volumes. Even if the mud fluid invasion or fines invasion extends beyond the volumes probed by two (or more) NMR measurements, it may still be possible to obtain information regarding different fluid saturations or fines invasion because the invasion process may generate a gradient of mud filtrate volume or free fluid volumes. As a result, at different distances from the wellbore, different amounts of native fluids are displaced by the invading mud filtrate or fines.

Accordingly, methods of the invention acquire two or more NMR measurements at different depth of investigation (DOI). In some embodiments, the depth of investigation (DOI) as used herein refers to the radial depth, i.e., the distance from the wellbore. The differences in fluid saturations (fluid compositions) as detected by these NMR measurements at different DOI are then used to determine whether hydrocarbons are present in the formation. The differences in fluid saturations may be detected by several methods. The following illustrates some of these methods. While the well may be drilled with either water-based mud or oil-based mud, the following description assumes a water-based mud. One skilled in the art would appreciate that the conclusions in the following description will need to be modified if an oil-based mud is used.

In some embodiments of the invention, the difference in fluid saturations at different depth of investigation is detected by porosity measurements. The apparent formation porosity (or fluid-filled porosity) may be determined from the initial NMR signal magnitudes (before $T_2$ decay), which are directly proportional to the amount of hydrogen present in the fluids existing in the volume probed by the NMR tool. In most formations, water is the wetting phase and oil is the non-wetting phase. Thus, water is more influenced by paramagnetic impurities on pore surfaces. As a result, water typically has shorter relaxation times (both $T_1$ and $T_2$) than those of light hydrocarbons. In a typical NMR logging, the polarization time (WT) may not be sufficiently long to allow all nuclear species to fully relax between pulse sequences. As a result, spins with longer $T_1$ (e.g., light oils) are not fully polarized and their signal amplitudes are suppressed relative to those of spins with shorter $T_1$ (e.g., water). Thus, a formation would appear to have a lower porosity when it is saturated with hydrocarbons. Based on this phenomenon, if the signal amplitudes (hence, apparent porosity) for the deeper measurements are lower than those for the shallower measurements, it is an indication of the presence of hydrocarbons with long $T_1$, e.g., gas, condensate, or light oil. It should be noted that the apparent porosity may be used to detect mud invasion if gas is present in the formation, irrespective of whether a water-based or oil-based mud is used. This is so because gas has a lower hydrogen index, and invasion of any mud filtrate, water or oil, will increase the hydrogen index in the shallow DOI regions.

In other embodiments of the invention, the differences in fluid saturations may be detected by polarization measurements. At each NMR depth of investigation (DOI), measurements with different polarization times (or wait time, WT) are acquired. NMR measurements with different polarization times (WT are sensitive to different longitudinal relaxation times ($T_1$) of different spin species. Different fluids (e.g., water or oil) in the formation typically experience different influence from their environments. For example, in smaller pores water phase often wets the surfaces of the pores, which may have paramagnetic impurities that facilitate spin relaxation (both longitudinal and transverse relaxations). In contrast, oil phase often exists as a non-wetting phase and is not influenced by surface relaxation. Consequently, different fluid components in the formation may have different $T_1$ relaxation times, and NMR measurements with $T_1$ contrast may be acquired with different WT. A measurement with long WT permits all fluid components (e.g., water and hydrocarbons) to be fully or substantially polarized by the magnetic field. On the other hand, a measurement with a short WT would only permit components with short $T_1$ (e.g., water) to be substantially polarized and detected.

Thus, the ratio of signal amplitudes for the long and short wait times $M_{short\_WT}/M_{long\_WT}$ may be used to provide information as to the type of fluids in the investigation zone. If the ratio $M_{short\_WT}/M_{long\_WT}$ is significantly lower for the deeper measurements, this is an indication of the presence of long $T_1$ species, such as light oil, condensate, or gas. One skilled in the art would appreciate that the difference, $M_{long\_WT} - M_{short\_WT}$, may alternatively be used instead of the ratio of these two measurements. In this case, if the difference is significantly greater at deeper DOI than at near wellbore region, then the presence of long $T_1$ species (e.g., light oil or gas) is indicated. While the above description uses the total signal amplitude, one skilled in the art would appreciate the ratio or difference of the two measurements may be based on the free-fluid amplitude.

Figure 3:
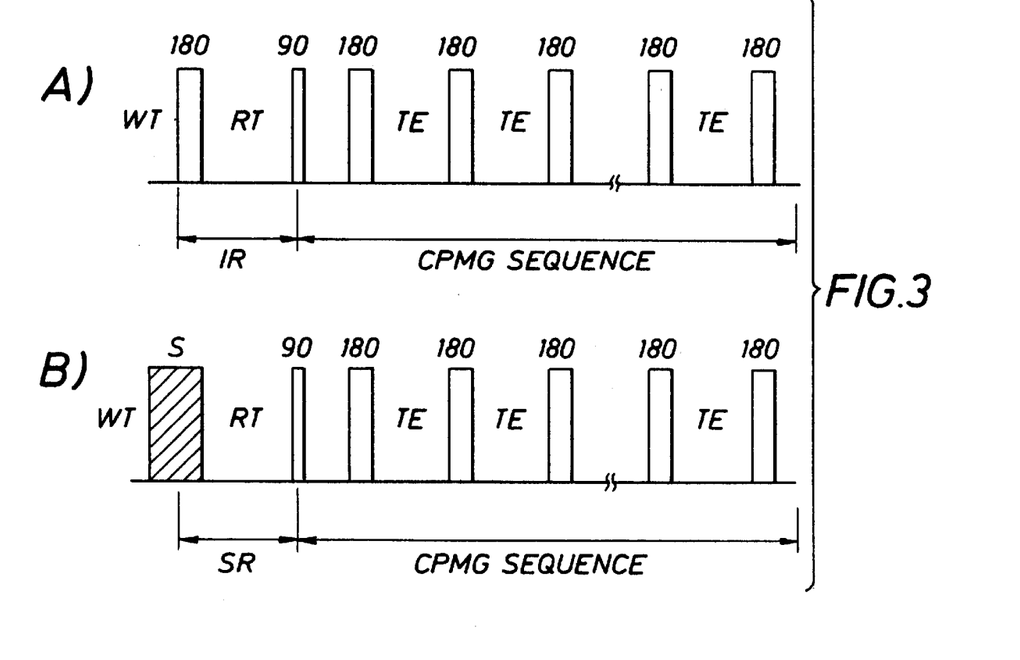
FIGS. 3A and 3B illustrate IR-CPMG and SR-CPMG pulse sequences, respectively.

NMR measurements with long and short WT may be acquired with CPMG pulse sequence or any of its variants. In addition, a CPMG pulse sequence may be used in combination with pulse sequences that specifically exploit $T_1$ relaxation. For example, an inversion recovery (IR) or saturation recovery (SR) sequence may be used in combination with a CPMG pulse sequence as illustrated in FIGS. 3A and 3B, which show an IR-CPMG and a SR-CPMG pulse sequences, respectively. Using these hybrid sequences, one would vary the recovery delay time (RT) instead of WT to obtain the T contrasts.

In other embodiments of the invention, the differences in fluid saturations may be detected by $T_1/T_2$ contrasts. Several methods are available for measuring $T_1/T_2$ ratios. The most common method involves repeated CPMG measurements in which the wait-time, or polarization time, is varied. Alternatively, measurements may be acquired at different logging speeds in separate runs of the tool. In this case, different effective polarization times are determined by the logging speed and the pre-polarization magnet length. Variations in the ratios or differences in calibrated signal amplitudes between the long and short effective polarization times for measurements at different DOI may be used to infer the presence of hydrocarbons.

In addition, the IR-CPMG and SR-CPMG pulse sequences as shown in FIGS. 3A and 3B may also be used to provide ratios of $T_1/T_2$. To obtain a ratio of $T_1/T_2$ NMR measurements are acquired with the RT and the inter-echo delay time (TE) varied between each measurement. In addition, the $T_1/T_2$ contrast may also be obtained using a typical CPMG pulse sequence. The difference in $T_1/T_2$ contrasts from measurements at different DOI may be used to infer the presence of hydrocarbons. As stated above, water in the formation tends to have shorter $T_2$ due to surface relaxivity. As a result, water typically has a $T_{1/T2} \geq 1.0$. On the other hand, hydrocarbons often are not in contact with the pore surface, and their $T_1/T_2$ ratios often approach 1. Thus, if the $T_1/T_2$ ratio at deeper DOI is smaller than that at near wellbore region, it can be inferred that the formation has hydrocarbons. Alternatively, higher $T_1/T_2$ ratios observed at deeper DOI may infer the presence of gas, since the $T_2$ of gas is usually reduced by the effects of fast diffusion in the field gradient.

Using IR-CPMG as an example, a pulse sequence for measuring the $T_1/T_2$ ratio would be: $(WT\ 180\ RT\ CPMG)_n$, as illustrated in FIG. 3A, where WT is the wait time (also called "polarization time") for spins to relax back to the steady state, RT is the recovery delay time during which the signals grow exponentially back to the steady state magnitudes, and CPMG is a typical CPMG pulse train.

With the IR-CPMG sequence, the first 180-degree pulse inverts the magnetization (i.e., onto the Z axis). After RT delay the signal may be detected with a 90-degree pulse. The signals are actually detected with a CPMG sequence as a train of spin echoes. The detected spin echo magnitudes will be influenced not only by the $T_2$ relaxation process (during the CPMG sequence), but also the $T_1$ relaxation process (during the IR sequence), which is encoded by the various RT delay times. FIG. 3B shows a CPMG sequence coupled with a saturation recovery (SR) sequence, instead of an inversion recovery (IR) sequence. This sequence is referred to as an "SR-CPMG" sequence. The SR-CPMG sequence as shown in FIG. 3B would detect signal components that have relaxed back to the Z axis after RT delay. The SR-CPMG may be used instead of the IR-CPMG in the embodiments of the invention.

In other embodiments, the differences in fluid saturations may be detected by diffusion methods. At each DOI, measurements with different inter-echo spacings (delays) are acquired. Ideally, the inter-echo spacings should be selected such that the products G×TE are similar for each DOI. With this parameterization, differences in the signal decay rate measured at different DOIs infers the presence of hydrocarbon. If the deeper measurements show an increased decay rate, this implies the presence of gas. Conversely, slower decay rates for the deeper DOI indicate the presence of intermediate viscosity oil. More generally, measurements with different TE values can be acquired at each DOI. In this case, differences in the change in decay rates with varying TE at each DOI may be used to infer the presence or absence of hydrocarbon.

While the diffusion measurements can be performed with a typical CPMG sequence with different inter-echo delay (TE), a new "diffusion editing"("DE") spin-echo sequence provides a better method. See M.D. Hürliman et al., "Diffusion-Editing: New NMR Measurement of Saturation and Pore Geometry ," paper presented at the 2002 Annual Meeting of the Society of Professional Well Log Analysts, Osio, Japan, Jun. 2–5; see also, PCT Published Application WO 01/42817 published on Jun. 14, 2001 by Hürlimann, entitled "Simpler and More Robust Hydrocarbon Typing with Pulsed NMR ." This application is assigned to the same assignee as the present invention and is hereby incorporated by reference.

Figure 4:
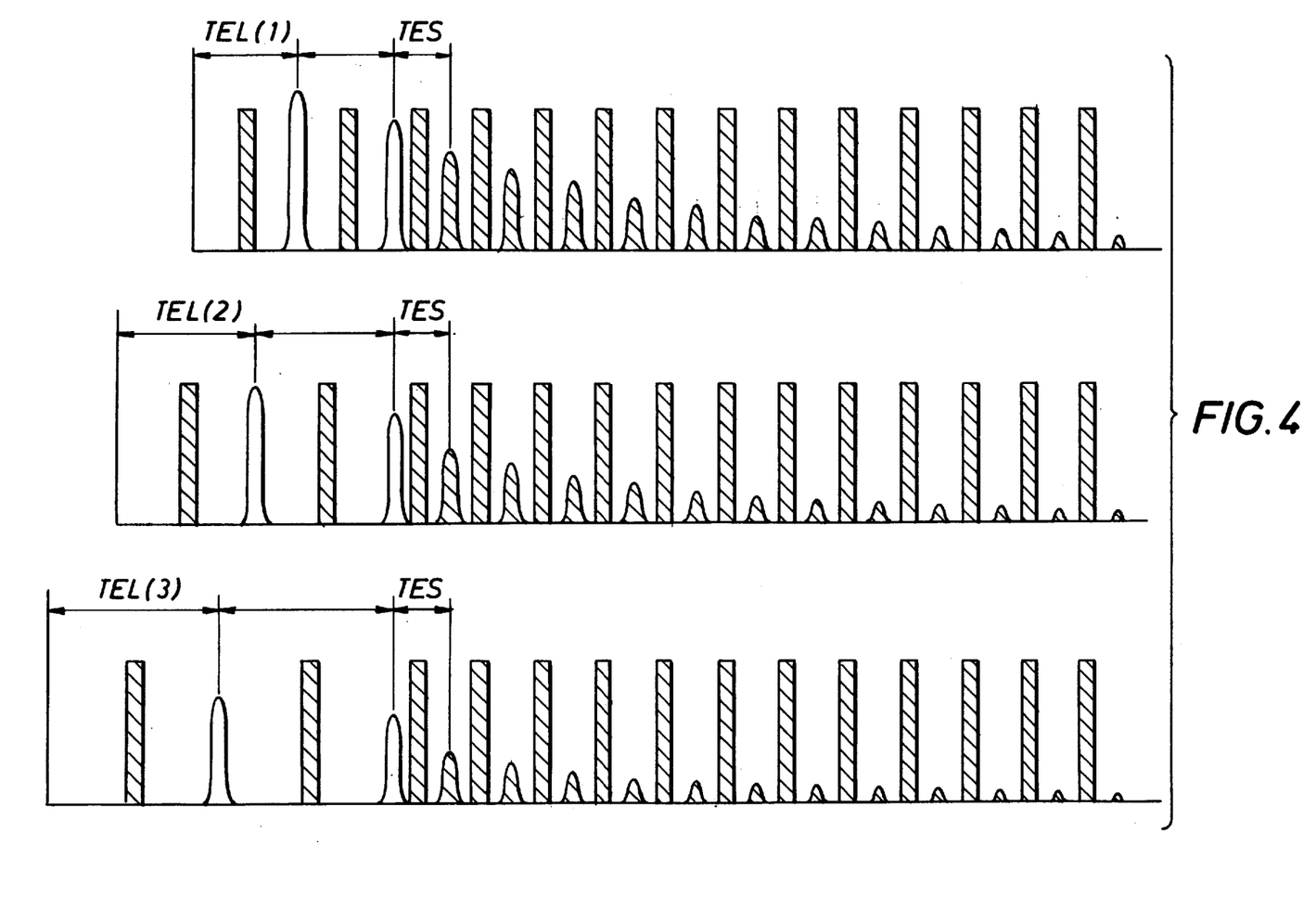
FIG. 4 illustrates diffusion-editing pulse sequences.

DE sequences (see FIG. 4) are similar to the CPMG sequences except that the initial two echoes are acquired with longer inter-echo delays and the third and subsequent echoes are acquired with shorter inter-echo delays. Diffusion information is encoded during the acquisition of the first two echoes, whereas the third and subsequent echoes provide bulk and surface relaxation time information at long acquisition times with little, if any, attenuation of the signal by diffusion. Although diffusion information is encoded during the acquisition of the first two echoes, as shown in FIG. 4, one skilled in the art would appreciate that other number (e.g., 1, 3, 4, etc.) of echoes may be used to encode the diffusion information.

Using a conventional CPMG sequence to encode the diffusion information requires a long inter-echo spacing, which results in poor bulk and surface relaxation time information because diffusion decay attenuates the signal after relatively few echoes. Consequently, a suite of data acquired with DE sequences provides diffusion information and better effective signal-to-noise ratio in the spin-echo data, as compared to an analogous suite acquired with CPMG sequences. DE sequences can provide more accurate and robust computations of component $T_2$ or diffusion (D) distributions than CPMG sequences can.

In other embodiments of the invention, the differences in fluid saturations may be detected by the MRF method or similar methods that can provide NMR parameters of individual components from measurements of a mixture of fluids. According to this method, MRF analysis is performed using a suite of NMR measurements at each DOI. From this analysis, fluid saturations and fluid properties are then evaluated. This approach would provide the most comprehensive data and quantitative analysis but may compromise logging speed.

The MRF method is a diffusion-based NMR fluid characterization method and can distinguish different components (e.g., oil and water) in a mixture of fluids (e.g., formation fluids) based on different molecular diffusion. NMR measurements with different sensitivities to diffusion may be acquired with several pulse sequences, including the CPMG pulse sequence or its variants, and the diffusion-editing (DE) pulse sequence. The MRF method takes advantage of the fact that decay of the transverse magnetization measured in a spin-echo experiment is due, in part, to molecular diffusion of the fluid molecules. Diffusion of molecules in an inhomogeneous static magnetic field causes the Larmor precession frequencies of the spins to become time dependent. This leads to imperfect refocusing of the spin-echo signals by the 180° pulses, and, therefore, to an irreversible diffusion-induced decay of the echoes.

The MRF method invokes a comprehensive and realistic relaxation model for reservoir fluids. Applying this model to appropriate suites of NMR data, MRF analysis can provide estimates for individual components in the formation fluids. These individual component estimates may provide information on, for example, flushed zone fluid saturations and oil viscosities. Initial results obtained with station logs acquired using current generation tools have demonstrated the potential of the MRF technique. See R. Freedman et al., "A New NMR Method of Fluid Characterization in Reservoir Rocks: Experimental confirmation and Simulation Results," SPEJ, (Dec., 2001), pp. 452–464; and R. Freedman et al.,"Field Applications of a New Magnetic Resonance fluid Characterization Method," paper SPE 71713 presented at the 2001 SPE Annual Technical Conference and Exhibition, New Orleans, Sep. 30–Oct. 3.

The above described are examples of NMR contrasts that may be used for the embodiments of the invention for the detection of mud filtrate invasion. One skilled in the art would appreciate that other NMR parameters may also be used. For example, the transverse relaxation times ($T_2$), which can be conveniently acquired with a CPMG-pulse sequence, can also be used as a contrast to compare NMR measurements acquired at different DOI. In addition, the differences in fluid saturations may be detected by combining different methods described above. For example, one may combine polarization and diffusion to provide contrasts at different DOI. Acquisition sequences combining polarization ($T_1$ contrast) and diffusion contrast could be devised using a relatively small number of individual measurements. By judicial choice of acquisition parameters, sequences may be devised that allow logging at moderate speeds.

Some embodiments of the invention relate to methods for detecting fines or whole mud invasion. Fines invasion physically plug pores in the formation. As a result, total NMR porosity will appear smaller in an invaded region (near wellbore region) as compared with that of a virgin region (a region far away from the wellbore). Fines invasion may be implicated if the porosity deficit (i.e., less porosity) is detected in the shallow (near) DOI measurements as compared with that of a deep DOI measurement.

Embodiments of the invention will now be illustrated with the following examples. The simplest case to consider is in a well drilled with water-base muds. Here, invasion of drilling fluids into the formation replaces some of the hydrocarbon and water in the near-wellbore region with water from the drilling mud. For a water-saturated formation, this displacement will not result in any detectible change. Therefore, the fluids sensed by NMR measurements at different DOI are essentially identical. On the other hand, in a hydrocarbon zone, displacement of the hydrocarbons by the water filtrate will be noticeable, and such displacement is more pronounced in the near wellbore region than in the deeper region. Therefore, NMR measurements at the near wellbore region have more contribution from the water filtrate, while the same measurements at the deeper region will have less contribution from the water filtrate.

TABLE 1

| | Acquisition sequence parameters used in simulations | | | | | | | | |
|---|---|---|---|---|---|---|---|---|---|
| Measurement Parameters | $WT_a$ (s) | $TE_a$ (rm) | $NE_a$ | $WT_b$ (s) | $TE_b$ (ms) | $NE_b$ | $WT_c$ (s) | $TE_c$ (ms) | $NE_c$ |
| Drop (20 G/cm) | 8 | 0.50 | 2000 | 0.50 | 0.50 | 2000 | 0.50 | 4.0 | 200 |
| Near (40 G/cm) | 8 | 0.25 | 4000 | 0.50 | 0.25 | 4000 | 0.50 | 2.0 | 400 |

Figure 5:
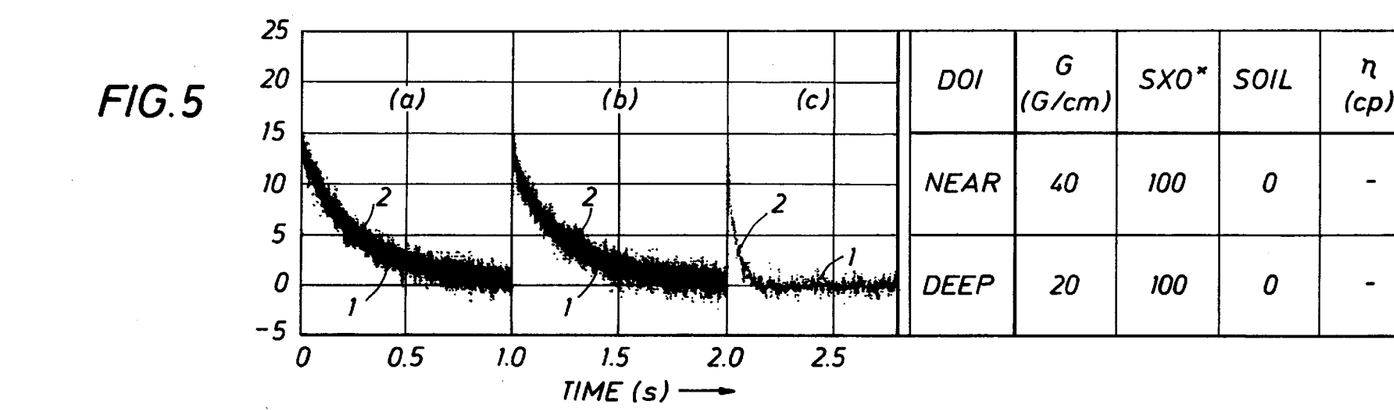
FIG. 5 shows results of simulations according to one method of the invention in a water-saturated zone in a well drilled with a water-based mud.
Figure 6:
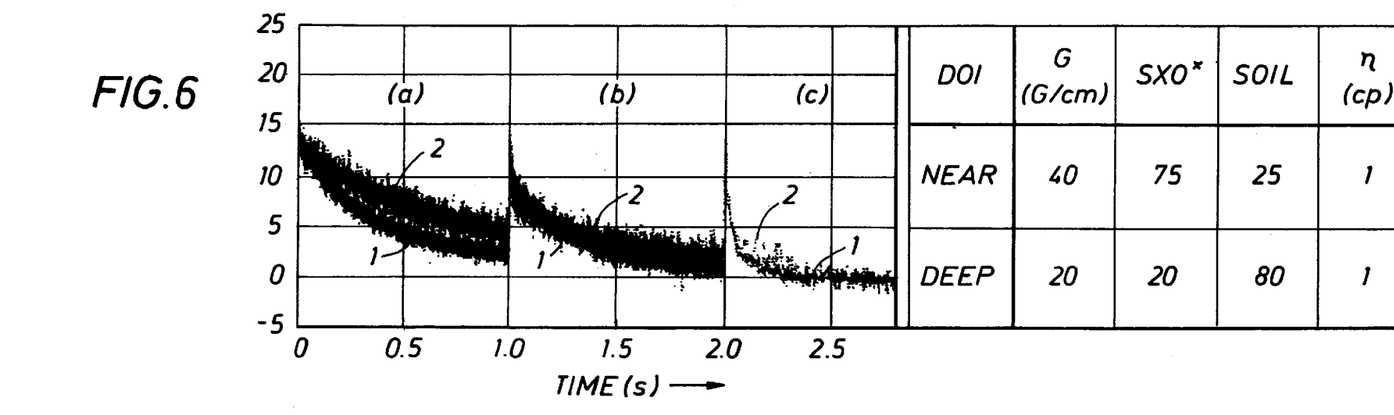
FIG. 6 shows results of simulations according to one method of the invention in an oil-saturated zone in a well drilled with a water-based mud.

WT, TE, and NE refer to polarization time, echo spacing, and number of echoes respective
Subscripts a, b and c correspond to the labels in FIGS. 5 and 6.

FIGS. 5 and 6 show the results of simulations of NMR responses in two different environments, water-saturated formation (FIG. 5) and hydrocarbon-saturated formation (FIG. 6). Acquisition parameters for the simulated sequences are shown in Table 1. In FIGS. 5 and 6, panels (a) are measurements with long WT, panels (b) are measurements from short WT, and panels (c) are measurements with long TE. Note that in each case, G×TE are identical for the corresponding near (curve 1) and deep (curve 2) measurements. The identical G×TE ensures that the diffusion effects between the two DOI measurements are identical or substantially similar so that other contrasts may be readily compared. Random Gaussian noise of 0.5 p.u./echo and 1.0 p.u./echo, respectively, were added to the simulated signals for the near (curve 1) and deep (curve 2) measurements. In each case, the formation porosity is 20 p.u. and includes a 6 p.u. signal from bound fluids with a $T_2$ distribution centered at 5 ms.

The simulations clearly show the different responses for the water-saturated formation (FIG. 5) and the oil zone (FIG. 6). Specifically, in the water-saturated zone, the responses from the two DOIs (curves 1 and 2) overlap (FIG. 5, panels (a)–(c)). This is expected because displacement of the formation water by filtrate water would not produce any detectable difference in NMR responses. In contrast, the responses from the near (curve 1) and deep (curve 2) measurements are clearly different in the hydrocarbon-saturated zone (FIG. 6). Again, this is expected because displacement of hydrocarbons by water filtrate should be more pronounced in the near wellbore region. Note that the difference in the NMR responses is more noticeable in panel (a) than in panels (b) and (c). Both panels (b) and (c) have short WT, which is not sufficient for most hydrocarbons to be fully polarized. Thus, the signals detected in panels (b) and (c) are probably mostly from the faster relaxation formation water, and, therefore, the differences between the near (curve 1) and deep (curve 2) measurements will be less.

Measurements in panel (a) of FIG. 6 were acquired with 8 second WT, which is sufficiently long for full polarization of most nuclear species. Thus, most species are detected in these two measurements (curves 1 and 2). It is clear from a comparison of curve 1 (near measurement) and curve 2 (deep measurement) that the deep measurement includes more long $T_2$ species, which are most likely hydrocarbons. In fact, the hydrocarbon simulation parameters were chosen to mimic a light (1 cp) oil. Thus, this is an example that $T_2$ contrast may be used to infer the presence of hydrocarbons using methods of the invention.

The situation with an oil-base mud is more complex. In this case, native oil may be completely or partially replaced by the oil filtrate. It is then necessary to detect differences between the two different types of hydrocarbons, rather than between hydrocarbons and water as in the case of water-based muds. Nevertheless, if there is sufficient difference in the compositions between the oil-based mud filtrate and the native hydrocarbon and that the different measured volumes have sufficiently different relative amounts of the native and drilling fluids, the technique is still applicable.

Figure 7:
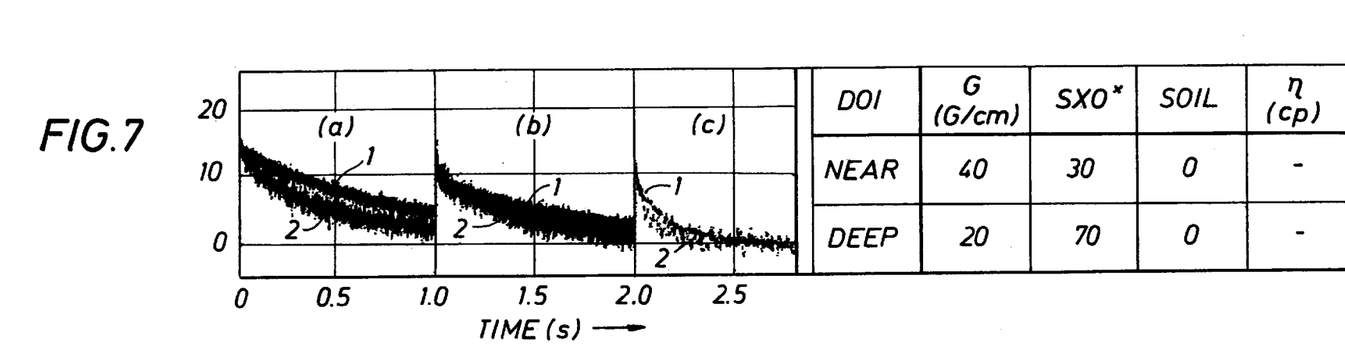
FIG. 7 shows results of simulations according to one method of the invention in a water-saturated zone in a well drilled with an oil-based mud.
Figure 8:
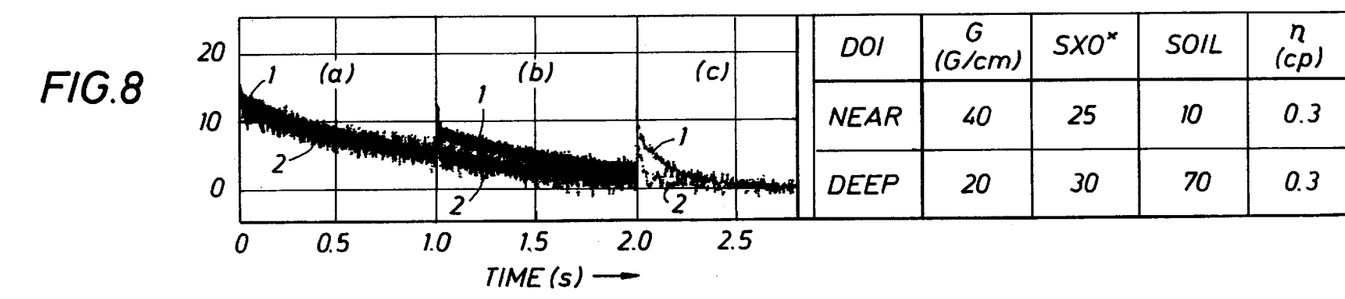
FIG. 8 shows results of simulations according to one method of the invention in a light oil zone in a well drilled with an oil-based mud.
Figure 9:
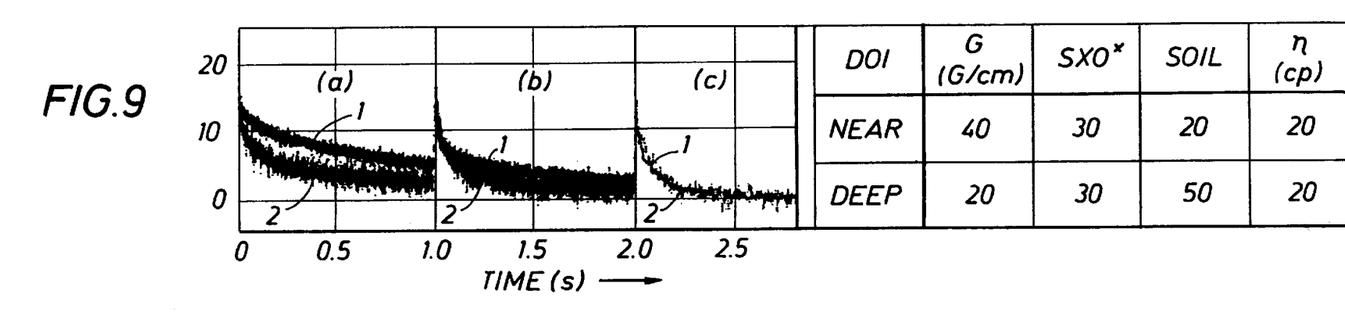
FIG. 9 shows results of simulations according to one method of the invention in a intermediate viscosity oil zone in a well drilled with an oil-based mud.

FIGS. 7–9 show the results of simulations of NMR responses at near (curve 1) and deep (curve 2) DOIs for three situations that might be encountered in wells drilled with oil-based muds: water zone, light oil zone, and intermediate viscosity oil zone, respectively. Acquisition sequence parameters are the same as those used in simulations shown in FIGS. 5 and 6 and are shown in Table 1.

FIG. 7 shows simulation results of a water zone. FIG. 8 show simulation results of a zone containing light oil (0.3 cp). FIG. 9 shows simulation results of a zone containing intermediate viscosity oil (20 cp). Again, panels (a), (b), and (c) correspond to simulations with long WT, short WT, and long TE, respectively. In each case, the formation porosity is 20 p.u. and includes a 6 p.u. of bound fluid having a $T_2$ distribution centered at 5 ms. For the hydrocarbon zone simulations (FIGS. 8 and 9), it was assumed that some residual oil remained in the near DOI volume and that the deep measurement sensed substantially higher oil saturations. Details of the fluid saturations and hydrocarbon viscosities are provided in the accompanying tables. The oil-based mud filtrate was modeled as a 1 cp oil with a narrow $T_2$ distribution.

FIG. 7 shows that the slowly decaying component for the deep measurement (curve 2) has a $T_1$ value comparable to or shorter than that for the near measurement (curve 1). This is apparent from a comparison between panel (a) and panel (b). From this result, it is predicted that this zone does not contain light hydrocarbon. Quantitative analysis of measurements (b) and (c) using the MRF method indicates that the hydrocarbon has a viscosity of approximately 1 cp, suggesting that the hydrocarbon signal may be due to the mud filtrate.

FIG. 8 shows that the slowly decaying component for the deep measurement (curve 2) has a $T_1$ value significantly greater than that for the near measurement (curve 1). This conclusion is drawn from the fact that the signal amplitude for the deeper measurement (curve 2) is significantly reduced relative to the near measurement (curve 1) in panel (b). From this we can infer the presence of light hydrocarbon or water in large pores (long $T_1$). This conclusion is further corroborated by measurements with long inter-echo delays (TE) shown in panel (c), which shows a rapid decay indicating that the fluid associated with the long relaxation times has a high diffusion constant. Distinguishing between light oil and large pore water is difficult on the basis of NMR data alone. However, in many cases of practical interest, large pores/vugs may be ruled out and the NMR responses such as these can then be interpreted in terms of light hydrocarbon. Alternatively, other measurements (e.g., resistivity) may be used in combination with the methods of the invention to distinguish between light oil and large pore water.

Referring to FIG. 9, on the basis of measurements shown in panels (a) and (b) alone, the NMR responses for this zone with intermediate viscosity oil resembles those for the water zone (FIG. 7). However, measurement in panel (c) indicates the presence of larger quantity of slow-diffusing fluid at the deep DOI. This observation is not compatible with a water zone, where a greater quantity of fast-diffusing fluid is expected at the deep DOI. A quantitative analysis of the data using the MRF method reveals a higher hydrocarbon viscosity for the deep DOI as compared with the near DOI (although total hydrocarbon saturation does not vary significantly). This result is consistent with the presence of an intermediate viscosity or heavy oil that has been partially flushed from the near DOI volume.

Figure 10:
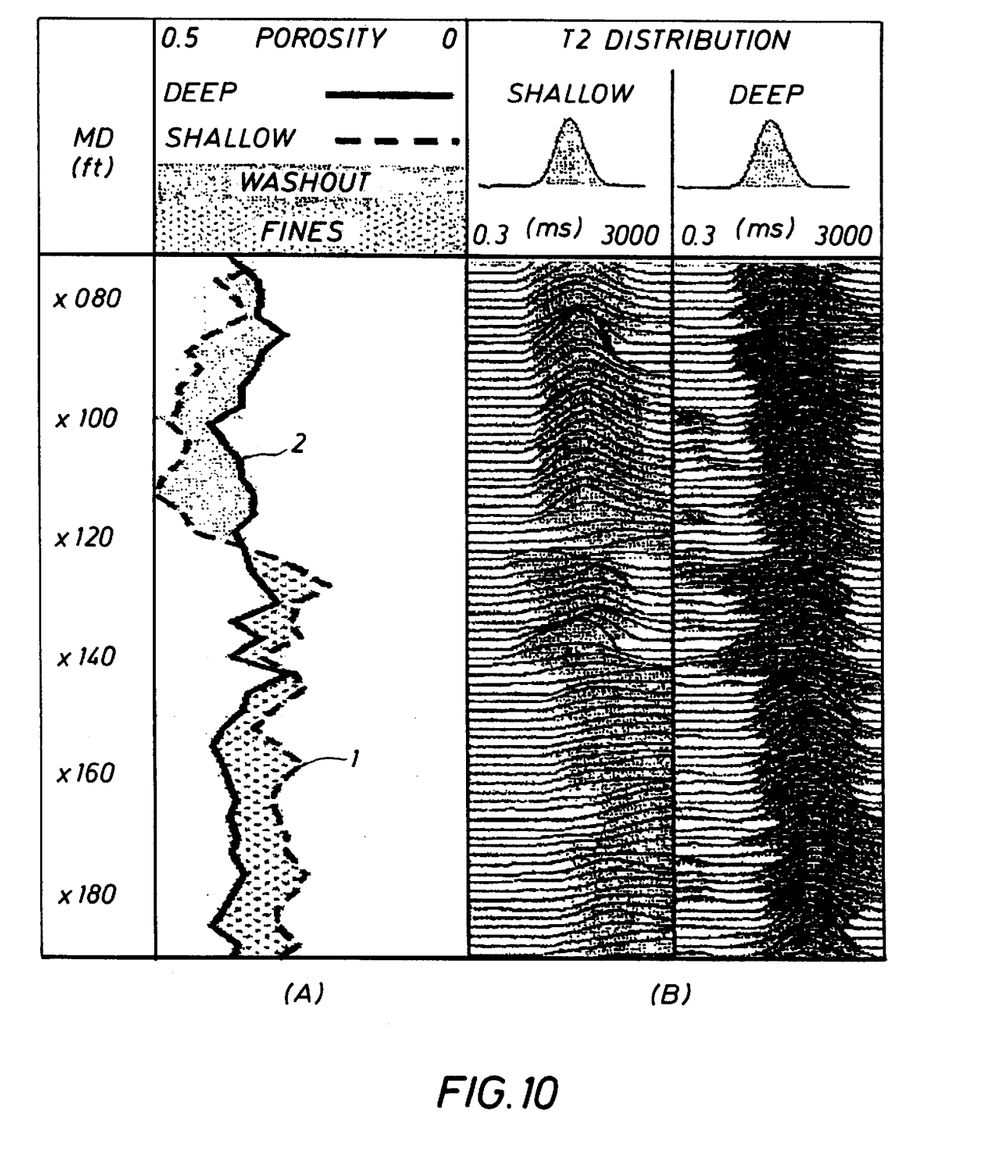
FIGS. 10A and 10B shows NMR porosity and $T_2$ distribution, respectively, obtained at different DOIs (shallow and deep) in a well according to a method of the invention.

FIGS. 10A 10B show results of a radial profiling of a well. The profiling was performed with a tool capable of multiple frequency acquisition. Two different frequencies were used to probe two DOIs (shallow and deep). FIG. 10A shows NMR porosity (curves 1 and 2 correspond to shallow and deep DOIs, respectively). It is apparent that at the lower half of the well, the porosity of the shallow measurement is significantly lower than that of the deep measurement, indicating fines invasion in the shallow DOI. Note that the top half of this well has washout, which shows up as a higher porosity in the shallow measurement because the shallow DOI "sees" the wellbore. FIG. 10B shows the $T_2$ distributions for the shallow and deep DOIs. Although the region having fines invasion seems to have more longer $T_2$ components, the magnitudes of the $T_2$ distribution in this region appear lower. In any event, a comparison between FIG. 10A and FIG. 10B suggests that porosity will be a more reliable indicator of fines invasion.

The above examples show that contrasts in fluid saturations may be detected and quantified by suites of NMR measurements conducted at different depths of investigation (DOI) and that from the observed contrasts, it is possible to infer the presence of hydrocarbons in the formation or to identify fines invasion. These examples show that contrasts in the transverse relaxation time ($T_2$), the longitudinal relaxation time ($T_1$) the ratio of longitudinal to transverse relaxation times ($T_1/T_2$), diffusion rates (D), or combination thereof can be used to detect variations in fluid saturations at different DOIs, while porosities and $T_2$ contrasts may be used to detect fines invasion. Any acquisition sequences, such as CPMG, diffusion editing pulse sequence, IR-CPMG, SR-CPMG, and others, that can probe variations in NMR responses can be used to obtain these contrasts.

While the above examples show that useful results may be obtained from comparison of NMR measurements without inversion, one skilled in the art would appreciate that the acquired measurements may also be inverted to provide NMR parameter (e.g., $T_1$, $T_2$, and $T_1/T_2$) distributions that can then be used to predict the presence of hydrocarbons in the formation. In particular, the MRF method, which is capable of providing NMR parameter distributions for individual fluid components, would be most useful in this regard.

Methods of the invention for detecting mud filtrate invasion are particularly useful in the case of wells drilled with water-based muds. In this case, any difference in NMR response detected at different DOIs infers the presence of hydrocarbon. With judicial choice of acquisition parameters, e.g., by constraining the product TE×G to be similar for corresponding measurements at different DOIs, diffusion effects may be normalized with respect to field gradient variations.

For oil-base muds, different scenarios (water zone, light oil zone, intermediate oil zone, gas) may be identified by comparing NMR responses from different DOIs with anticipated response for different scenarios. Quantitative analysis of the data for example using MRF may be used to help interpret the responses.

Figure 11:
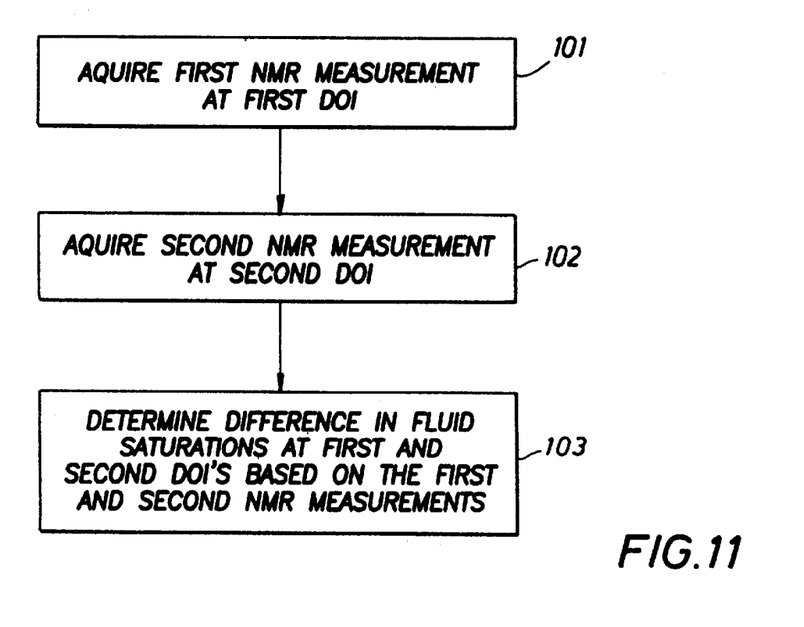
FIG. 11 shows a flow chart of a method according to one embodiment of the invention.

FIG. 11 shows a flow chart of a method according to one embodiment of the invention. First, an NMR measurement at the first DOI is acquired (shown as 101). The acquisition may use any pulse sequences suitable for the desired contrast (e.g., $T_1$, $T_2$, $T_1/T_2$, or D). These pulse sequences include those described above: CPMG or its variant, DE pulse sequence, IR-CPMG, and SR-CPMG. Next, another NMR measurement is acquired at the second DOI, using the same pulse sequence and similar acquisition parameters (shown as 102). It is preferred that the acquisition parameters be kept the same for the first and the second NMR measurements, except for the inter-echo delay (TE), which is preferably varied such that the product G×TE is identical for the two measurements. As sated above, this is to normalize the effects of diffusion at different gradients and to facilitate comparison between the two NMR measurements. However, the method is also applicable if the product G×TE is not identical for the measurements at different DOI. For detecting fines invasion, it is preferred that the first and the second NMR measurements use the same parameters such that the magnitudes of the measurements may be directly used to derive the total NMR porosity or free fluid volumes, or the $T_2$ distributions. Although FIG. 11 shows a minimal scheme involving only two measurements at two different DOIs, one skilled in the art would appreciate that more than two measurements may be used to achieve the same purpose.

Once these measurements are available, they are compared to see if there is any difference in fluid saturations (fluid compositions) or contrast of the selected NMR response parameter (e.g., NMR porosity, free fluid volume, $T_1$, $T_2$, or D) at the different DOIs (shown as 103). Again, the comparison may be based on the measurement data (e.g., the spin-echo train) without inversion. Alternatively, these measurement data may be inverted to provide the NMR response parameter (e.g., $T_1$, $T_2$, $T_1/T_2$, and D) distributions for comparison. The inversion may include using the MRF method ("magnetic resonance fluid characterization methods").

Any difference in fluid saturations is then used to infer the presence of hydrocarbons in the formation as illustrated in FIGS. 5–9, and any free fluid volume difference or $T_2$ distribution difference may be used to infer the presence of fines invasion. Specific interpretation of any difference in fluid saturations would certainly depend on the type of drilling mud used and may also depend on the expected formation properties.

Although detection of contrasts of NMR measurements at different DOI with methods of the invention may be taken as a reliable indication that hydrocarbon is present, failure to detect contrasts does not necessarily imply the absence of hydrocarbons. Many factors can contribute to such failure. For example, efficient flushing of the entire range of NMR volumes will give rise to zero or reduced contrast between different DOIs. Similarly, extremely shallow or hindered invasion (heavy oil, tar, bitumen) could also give rise to low contrast between different DOIs.

While the invention has been described with respect to a limited number of embodiments, those skilled in the art, having the benefit of this disclosure, will appreciate that other embodiments can be devised which do not depart from the scope of the invention as disclosed herein. For example, while embodiments of the invention are illustrated with only two DOI measurements in the above examples, one skilled in the art would appreciate that multiple DOI measurements may be used. In addition, embodiments of the invention may be practiced with a wireline tool as well as a LWD or MWD tool. Furthermore, embodiments of the invention may be combined with other types of measurements. Accordingly, the scope of the invention should be limited only by the attached claims.

What is claimed is:

1. A method for detecting hydrocarbon-bearing zones in a formation penetrated by a wellbore, comprising:
   acquiring at least two nuclear magnetic resonance measurements, each of the at least two nuclear magnetic resonance measurements acquired from a volume of investigation at a different radial depth from the wellbore; and
   determining whether the formation bears hydrocarbons by comparing the at least two nuclear magnetic resonance measurements.

2. The method of claim 1, wherein the acquiring the at least two nuclear magnetic resonance measurements uses a pulse sequence selected from a Carr-Purcell-Meiboom-Gill pulse sequence, a diffusion-editing pulse sequence, an inversion recovery Carr-Purcell-Meiboom-Gill pulse sequence, and a saturation recovery Carr-Purcell-Meiboom-Gill pulse sequence.

3. The method of claim 2 wherein the each of the at least two nuclear magnetic resonance measurements is acquired with substantially identical parameters except for an inter-echo delay time.

4. The method of claim 3, wherein a product of the inter-echo delay time and a magnetic field gradient at the volume of investigation is substantially identical for the each of the at least two nuclear magnetic resonance measurements.

5. The method of claim 1, wherein the comparing the at least two nuclear magnetic resonance measurements comprises deriving distributions of at least one nuclear magnetic resonance parameter.

6. The method of claim 5, wherein the at least one nuclear magnetic resonance parameter comprises one selected from a longitudinal relaxation, a transverse relaxation, a ratio of longitudinal relaxation and transverse relaxation, an apparent porosity, and a diffusion constant.

7. The method of claim 5, wherein the deriving involves a magnetic resonance fluid characterization method.

8. The method of claim 1, wherein the comparing the at least two nuclear magnetic resonance measurements comprises:

deriving an apparent porosity from the each of the at least two nuclear magnetic resonance measurements; and comparing the apparent porosity from the each of the at least two nuclear magnetic resonance measurements.

9. The method of claim 1, wherein the determining comprises deriving a fluid saturation for the each of the at least two nuclear magnetic resonance measurements.

10. The method of claim 9, wherein the formation is drilled with a water-based mud.

11. The method of claim 10, wherein a difference in the fluid saturation for the each of the at least two nuclear magnetic resonance measurements indicates a presence of hydrocarbons in the formation.

12. The method of claim 1, wherein the formation is drilled with a water-based mud.

13. The method of claim 1, wherein the formation is drilled with an oil-based mud.

14. A method for nuclear magnetic resonance logging of a formation penetrated by a wellbore, comprising:

providing a nuclear magnetic resonance instrument moveable in the wellbore;

acquiring at least two nuclear magnetic resonance measurements, each of the at least two nuclear magnetic resonance measurements acquired at a volume of investigation at a different radial depth from the wellbore; and determining whether the formation bears hydrocarbons by comparing the at least two nuclear magnetic resonance measurements.

15. The method of claim 14, wherein the acquiring the at least two nuclear magnetic resonance measurements uses a pulse sequence selected from a Carr-Purcell-Meiboom-Gill pulse sequence, a diffusion-editing pulse sequence, an inversion recovery Carr-Purcell-Meiboom-Gill pulse sequence, and a saturation recovery Carr-Purcell-Meiboom-Gill pulse sequence.

16. The method of claim 15 wherein the each of the at least two nuclear magnetic resonance measurements is acquired with substantially identical parameters except for an inter-echo delay time.

17. The method of claim 16, wherein a product of the inter-echo delay time and a magnetic field gradient at the volume of investigation is substantially identical for the each of the at least two nuclear magnetic resonance measurements.

18. The method of claim 14, wherein the comparing the at least two nuclear magnetic resonance measurements comprises deriving distributions of at least one nuclear magnetic resonance parameter.

19. The method of claim 18, wherein the at least one nuclear magnetic resonance parameter comprises one selected from a longitudinal relaxation, a transverse relaxation, a ratio of longitudinal relaxation and transverse relaxation, an apparent porosity, and a diffusion constant.

20. The method of claim 18, wherein the deriving involves a magnetic resonance fluid characterization method.

21. The method of claim 14, wherein the comparing the at least two nuclear magnetic resonance measurements comprises deriving a fluid saturation from the each of the at least two nuclear magnetic resonance measurements.

22. The method of claim 14, wherein the comparing the at least two nuclear magnetic resonance measurements comprises:

deriving an apparent porosity from the each of the at least two nuclear magnetic resonance measurements; and comparing the apparent porosity from the each of the at least two nuclear magnetic resonance measurements.

23. A method for detecting fines invasion in a formation surrounding a wellbore, comprising:

acquiring at least two nuclear magnetic resonance measurements, each of the at least two nuclear magnetic resonance measurements acquired from a volume of investigation at a different radial depth from the wellbore; and determining whether the fines invasion has occurred by comparing the at least two nuclear magnetic resonance measurements.

24. The method of claim 23 wherein the at least two nuclear magnetic resonance measurements are acquired with substantially identical parameters.

25. The method of claim 23, wherein the comparing the at least two nuclear magnetic resonance measurements comprises deriving one parameter selected from the group consisting of free fluid volumes, porosity, and bound fluid volume.

26. The method of claim 23, wherein the comparing the at least two nuclear magnetic resonance measurements comprises deriving transverse relaxation time distributions.

* * * * *